United States Patent [19]

Duflot

[11] Patent Number: 5,573,794
[45] Date of Patent: Nov. 12, 1996

[54] PROCESS FOR TREATING A SOLUBLE GLUCOSE POLYMER AND PRODUCT THUS OBTAINED

[75] Inventor: Pierrick Duflot, Richebourg, France

[73] Assignee: Roquette Freres, Lestrem, France

[21] Appl. No.: 345,827

[22] Filed: Nov. 21, 1994

[30] Foreign Application Priority Data

Nov. 22, 1993 [FR] France ................... 93 13943

[51] Int. Cl.$^6$ .................................... A23L 1/015
[52] U.S. Cl. ............... 426/48; 426/271; 426/658;
426/660; 426/804; 127/46.2; 435/95; 435/96; 435/101
[58] Field of Search .................. 426/658, 271, 426/804, 48, 660; 127/46.2; 435/14, 25, 22, 95, 96, 99, 101; 536/127, 18.5, 18.6

[56] References Cited

U.S. PATENT DOCUMENTS

| | | | |
|---|---|---|---|
| 2,436,967 | 3/1948 | Leuck | 260/209 |
| 2,719,179 | 9/1955 | Mora | 260/209 |
| 3,766,165 | 10/1973 | Rennhard | 260/209 R |
| 4,622,233 | 11/1986 | Torres | 426/548 |
| 4,904,774 | 2/1990 | McDaniel et al. | 536/127 |
| 4,965,354 | 10/1990 | Yanaki et al. | 536/124 |
| 4,978,751 | 12/1990 | Biton et al. | 536/123 |
| 5,051,500 | 9/1991 | Elmore | 536/50 |
| 5,091,015 | 2/1992 | Bunick et al. | 127/46.2 |
| 5,094,951 | 3/1992 | Rosenberg | 435/190 |
| 5,366,962 | 11/1994 | Biton et al. | 514/54 |

FOREIGN PATENT DOCUMENTS

| | | |
|---|---|---|
| 0 289 461 | 11/1988 | European Pat. Off. . |
| 0 342 156 | 11/1989 | European Pat. Off. . |
| 0 368 451 | 5/1990 | European Pat. Off. . |
| 0 380 248 | 8/1990 | European Pat. Off. . |
| 0 458 748 | 11/1991 | European Pat. Off. . |
| 0 473 333 | 3/1992 | European Pat. Off. . |
| WO92/12179 | 7/1992 | WIPO . |
| WO92/14761 | 9/1992 | WIPO . |

OTHER PUBLICATIONS

Database WPI Week 8512, Derwent Publications Ltd., London, GB; AN 85-072246 & JP-A-60 027 365 (Nippon Shokuhin) 12 Février 1985 * abrégé *.
Patent Abstracts of Japan vol. 12, No. 33 (C-472) 30 janvier 1988 & JP-A-62 180 787 (Ishimura Fumihiro) 8 août 1987 *abrégé*.

Primary Examiner—Esther Kepplinger
Assistant Examiner—Lien Tran
Attorney, Agent, or Firm—Henderson & Sturm

[57] ABSTRACT

A process for purifying glucose polymers which consists in treating a low-calorie soluble glucose polymer: polyglucose, polydextrose or pyrodextrin, with a glucose oxidase and an anion exchanger in hydroxyl form. It enables largely colourless products having little or no bitterness, high viscosities and little hygroscopicity to be obtained. The products obtained may be used as sugar substitutes or fat substitutes.

10 Claims, No Drawings

PROCESS FOR TREATING A SOLUBLE GLUCOSE POLYMER AND PRODUCT THUS OBTAINED

BACKGROUND OF THE INVENTION

1. Field of the Invention

The present invention relates to a process for the purification of a low-calorie soluble glucose polymer. More precisely, it relates to a process for the purification of a polydextrose or of a polyglucose or of a pyrodextrin, consisting in treating the polydextrose, or the polyglucose or the pyrodextrin, using glucose oxidase and an anion exchanger in hydroxyl $OH^-$ form.

2. Description of the Prior Art

It is known that glucose, optionally mixed with polyols, may be polymerized under hot conditions in the presence of inorganic or carboxylic acids, according processes which have been described, for example, in U.S. Pat. Nos. 2,436,967, 2,719,179 and 4,965,354 as regards the inorganic acids or U.S. Pat. Nos. 3,766,165 and 5,051,500 as regards the carboxylic acids.

The soluble polyglucoses obtained, composed mainly of 1–6 glucose-glucose linkages and of atypical 1–2 and 1–3 glucose-glucose linkages, are difficult to digest.

Their low caloric value, which is generally thought to be in the region of 4.18 kilojoules/gram (equivalent to 1Cal/g), and their technological properties which are close to those of sucrose make them candidates for the replacement of this sugar as filling agents, inert products which are very much sought after as dietary fibre.. They also possess physical properties which enable them to substitute for certain fats and thereby to reduce the caloric power thereof drastically.

However, the organoleptic properties of the polymers thus obtained do not permit them to find the widest possible use in food products.

The reason for this is that these crude polymers are still coloured or acidic or bitter, which does not allow them to be used in the total replacement of sugar or of fats and which limits their application to products such as fruit juices, which already have a certain coloration, acidity and bitterness.

In addition, as a result of the presence of free glucose, and to a lesser extent of free sorbitol, in these crude polymers, these products are not as low in calories as possible.

The persistence of free glucose or of free sorbitol in these polymers also gives rise to other drawbacks, such as the existence of a sweet taste, which is incompatible with fats, and results, moreover, in a reducing of the equilibrium viscosity and relative humidity of the polymers obtained or of the products in which they are incorporated as sugar substitutes.

Numerous attempts have already been made to provide these polymers with the qualities which they lack.

Thus, it has been proposed to purify polydextrose (glucose polymer, or polyglucose, obtained most generally condensation of glucose in the presence of sorbitol and citric acid) by decolouring it using peroxides and then by precipitating it via organic solvents, so as to liberate it from the free glucose, sorbitol and citric acid, as well as from levoglucosan which would impart a bitter taste thereto. An account of this process has been given in U.S. Pat. No. 4,622,233. However, the amounts of solvent to be used are enormous and the process is thus not satisfactory from the points of view of economy and safety.

Another process for purifying polydextrose, an account of which is given in European Patent Application No. 289,461, consists in removing the coloured and bitter impurities therefrom by extraction using organic solvents, but without precipitating the polymer. In this case also, the amounts of solvent to be used are enormous, and this process therefore suffers from the same drawbacks of economy and safety.

European Patent Application No. 342,156 proposes to remove the low-molecular-weight compounds present in the crude polydextrose, which are essentially glucose, sorbitol,, citric acid and levoglucosan, by reverse osmosis and diafiltration. The process is expensive since, in this case., it requires enormous amounts of water in order to perform the osmosis and then the diafiltration and, in addition, the strongly coloured large molecules are not removed and contribute towards the poor appearance of the product obtained.

European Patent Application No. 380,248 proposes to treat polydextrose with adsorbent or weak anionic resins so as to lower the free and esterified citric acid content thereof and claims thus to enhance the taste thereof. The product obtained still contains, however, low-molecular-weight caloric compounds such as glucose and sorbitol, and it is not rid of all bitterness or of coloration.

European Patent Application No. 458,748 proposes a similar process to the above, using anionic celluloses, and also leads to a product having the same drawbacks.

European Patent Application No. 473,333, via a 20 process using several ion-exchange resins of differing functionalities, claims that it lowers the residual levels of free and esterified citric acid in the polydextrose to the limit of detection, and asserts that a product of reduced bitterness is thus obtained. However, the product obtained still contains low-molecular-weight caloric compounds such as glucose and sorbitol and it is still coloured. This specific polydextrose is marketed by the company Pfizer under the brand name LITESSE® II.

PCT Patent Application WO 92/12179, via a process of molecular sieving on cationic resins that retains the compounds of low molecular weight, makes it possible to obtain a product similar to that obtained by the process outlined in European Patent Application No. 342,156 already cited above. However, just as in this patent application, the process is expensive since molecular sieving requires a large amount of water. Moreover, the strongly coloured large molecules are not separated from the polymer either, and contribute towards the poor appearance of the product obtained.

PCT Patent Application WO 92/14761 proposes a polydextrose or a polyglucose (low-calorie soluble glucose polymer obtained by the action of inorganic acids on glucose) containing only a small amount of reducing glucose groups. Such a product is obtained especially by catalytic hydrogenation of a polydextrose or polyglucose solution. The product obtained is largely colourless, but is not as low in calories as possible since it contains sorbitol originating from the hydrogenation of the free glucose contained in the polydextrose or the polyglucose as well as the free sorbitol already present in the polydextrose.

European Patent application No. 368,451 proposes treat a pyrodextrin with a starch hydrolysis enzyme such as alphaamylase, for the purpose of deodorizing it and of removing the unpleasant taste therefrom so that it may serve as dietary fibre. A pyrodextrin is a low-calorie soluble glucose polymer obtained by dry-roasting starch containing, as in polyglucose or polydextrose, atypical 1–2 and 1–3 glucose-glucose linkages, but mainly containing standard starch 1–6 linkages and especially 1–4 linkages, making this product digestible to an extent of about 50%, which thus imparts a caloric value of 8 Kjoules/gram (equivalent to 2 Cal/g).

U.S. Pat. 5,094,951 describes the production of glucose oxidase by a genetically recombined yeast: *Saccharomyces cerevisiae*. *Glucose oxidase* (EC 1.1.3.4) is the enzyme which catalyses the oxidation of glucose into gluconic acid with concomitant production of hydrogen peroxide. This enzyme has many industrial applications, among which there may be noted its use for removing glucose from egg white or from egg yolk before drying them, the aim being to avoid Maillard browning reactions, for removing residual glucose from syrups with a high fructose content, for removing dissolved oxygen contained in drinks, moist food products, perfumes when these are contained in leakproof packaging, and for assaying glucose in industrial products and in biological fluids such as blood and urine.

Bearing in mind that there is a growing interest in good-quality soluble food fibres which are largely colourless, as taste-free as possible and also as low in calories as possible, the Applicant Company has carried out much research with the aim of developing an economic process which enables such a quality of fibres to be obtained.

SUMMARY OF THE INVENTION

In a manner which is extremely simple and particularly effective compared with all that has been hitherto proposed, the Applicant Company has observed that such fibres could be readily obtained by subjecting a low-calorie soluble glucose polymer to a purification process comprising the action of a glucose oxidase, followed by treatment of the product obtained with an anion exchanger in hydroxyl form.

Despite its simplicity, the process proposed surprisingly enables soluble glucose polymers to be highly decolorized and enables virtually all of the acrid and burnt taste to be removed therefrom. By removing the free glucose, it also contributes towards lowering the caloric content of the soluble fibres obtained, as well as enhancing the thermal stability thereof and increasing the equilibrium viscosity and relative humidity thereof.

The Applicant believes that the production of hydrogen peroxide and the increasing presence of oxygen which occur during the oxidation of glucose into gluconic acid could play a role in this phenomenon. Oxidants such as hydrogen peroxide, benzoyl peroxide or sodium chlorite have indeed already been used to decolorize polydextrose before precipitating it with solvents, as has already been indicated in U.S. Pat. No. 4,622,233.

Although the product obtained by the treatment with glucose oxidase does not appear absolutely decolorized, the Applicant has noticed that the subsequent treatment on anion exchangers enables it to be decolorized much more readily than if it has not undergone this enzymatic treatment. In addition, the anion exchange which takes place on the exchanger enables the gluconic acid, which was formed at the expense of the glucose, to be bound, the enzymatic treatment combined with the anion exchange thereby contributing to the lowering of the calorific content of the polydextrose or of the polyglucose which have undergone this treatment. Another advantage of the process according to the invention, residing in the removal of the free glucose, is that it enables products which are not cariogenic to be obtained, when these are confections, such as candies, or low-calorie margarines freed of any foreign taste when this product is used in partial substitution for the fats.

This decrease in the free glucose content of the products obtained also has the consequence of increasing the average molecular mass, both the weight-average and the number-average masses (Mw and Mn) of the polymers obtained and contributes towards imparting a lesser hygroscopicity thereto and towards increasing the thermal stability thereof, and the equilibrium relative humidity and viscosity thereof.

DESCRIPTION OF THE PREFERRED EMBODIMENTS

The process proposed by the present invention may also comprise even more preferred embodiments, which consist, for example, in subjecting:

the low-calorie soluble glucose polymer to the action of starch-hydrolysing enzymes, prior to its purification according to the process of the invention. This prior enzymatic hydrolysis, which may also be carried out in the presence of glucose oxidase, enables soluble polymers which are particularly low in calories, completely acariogenic and of particularly high molecular weight to be obtained, the low-calorie soluble glucose polymer to a catalytic hydrogenation, subsequent to its purification, according to the process of the invention. This subsequent catalytic hydrogenation enables soluble polymers which are substantially colourless, heat-stable and completely neutral from the taste and odour points of view to be obtained.

Obviously, these complementary treatments may both be carried out, thus providing their respective contributions to the qualities of the products obtained.

The process of the invention makes it possible to purify and to enhance polydextrose greatly when this producer is used, but the Applicant prefers, however, to apply it to a polyglucose obtained solely with the use of glucose and inorganic acid.

To the knowledge of the Applicant, such glucose polymers are not commercially available, but are preferred as starting materials in the context of obtaining the products according to the invention as they are obtained very economically.

These polyglucoses have much more pronounced colorations and tastes than those of polydextrose, but the process of the invention makes it surprisingly possible to accommodate this handicap readily. These polyglucoses have, however, the advantage of not containing free sorbitol contributing to the caloricity of the product, which free sorbitol would not be removed by the process of the invention.

These polymers are conveniently obtained by heating and melting dextrose (crystalline glucose) in the presence of 5 to 500 parts per million by weight of sulphuric acid. This molten mixture is then maintained at a temperature of between 140 and 195° C. under reduced pressure in order to remove the reaction water, and this cooking is continued until a DE (dextrose equivalent) of between about 6 and 15 is obtained.

This residual reducing power is due to the presence of free glucose in the polymer, but also to the existence of hemiacetal reducing extremities present at the ends of the polymer chain thus formed.

When use is made of a more preferred process of the invention which, prior to the steps of enzymatic oxidation and of deacidification-decolorization on anion exchangers or at the same time as the step of enzymatic oxidation and prior to the step of deacidification-decolorization on anion exchangers, uses a step of hydrolysis of the glucose polymer with the aid of starch-hydrolysing enzymes, it is possible to use alpha-amylase, amyloglucosidase, iso-amylase, pullulanase or beta-amylase, these enzymes being used alone, successively or as a mixture. For reasons of cost, simplicity and effectiveness, it is preferred to make use only of amyloglucosidase.

The amounts and the conditions of action of the various enzymes which may be used for this preliminary step of enzymatic hydrolysis of the glucose polymers are, for example, as follows and are generally those which are recommended for the hydrolysis of starch:

amyloglucosidase: 4000 to 400,000 international units, temperature of 50 to 60° C., duration of action of from 30 to 72 hours, pH of 5.0 to 6.0, alpha-amylase: 20 to 2000 KNV units (kilo Novo Units) per kilogram of dry substrate, temperature of 50 to 60° C., duration of action 16 to 30 hours.

The enzymes used may be bacterial, fungal or vegetable in nature.

When another more preferred process of the invention makes use, subsequent to the steps of enzymatic oxidation and of deacidification-decolorization on anion exchangers:, of a step of catalytic hydrogenation of the glucose polymer, this hydrogenation is preferably carried out using Raney nickel at a temperature in the region of 130 to 140° C., at a pH between 4.0 and 8.0, preferably in the region c,f 7.0, and at a hydrogen pressure of between 20 and 200 bar, preferably in the region of 50 bar.

The hydrogenation, the duration of which is inversely proportional to the amount of catalyst used, is carried out at a concentration of the aqueous solution of the glucose polymer which is between 20 and 75%, preferably in the region of 40%, until a percentage of residual reducing sugars of less than 0.5%, preferably of less than 0.25% and even more preferably of less than 0.15%, is obtained.

The hemiacetal extremities present at the ends of the polymer chain are then reduced down to primary alcohol functions and sorbitol molecules are thus found at the ends of the polymer, these molecules being covalently bonded thereto and not participating as such in the caloric content or in the lowering of the molecular weights of the polymers obtained. This quasi-absence of residual reducing sugars imparts very great thermal stability to the polymers thus obtained.

After the hydrogenation, the product is demineralized in order to remove the traces of soluble nickel and the acids which are formed by the unwanted Cannizarro side-reaction.

as regards the process more generally claimed for the purification of the soluble glucose polymer, which makes use of a step of enzymatic oxidation followed by a step of deacidification-decolorization on an anion exchanger, a crude enzymatic composition of glucose oxidase also containing catalase is preferably used for the enzymatic oxidation.

Glucose oxidase catalyses the following reaction:

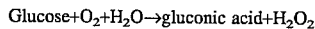

Catalase converts the hydrogen peroxide thus produced according to the reaction:

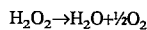

Such an enzymatic composition is available, for example, from the company NOVO, Denmark under the name SP 358.

This enzymatic oxidation must take place in an aerated medium and the pH of such a medium is preferably maintained at a value between 3.5 and 8.0, preferably between 4.0 and 7.0 and even more preferably between 5.0 and 6.0.

The concentration of glucose polymer is not critical and may range from 5 to 75%. However, high polyglucose concentrations make it necessary as work proceeds to adjust the pH using a base or to carry out the oxidation in the presence of a buffer salt such as calcium carbonate. Stabilization of the pH at a value between 5.0 and 6.0 has, however, the advantage of allowing the simultaneous action of an amyloglucosidase but, in this case, these cations ought subsequently to be removed either by precipitating them and filtering them off in the form of insoluble oxalate salt for example, or by binding them to a cation exchanger. For economic reasons, it is preferred, however, to carry out the oxidation on aqueous solutions containing about 30 to 50% of solids content. The teduperature may be adjusted within a wide range of from 15 to 70° C. but, for convenience, it is preferred to work at around 30°–40° C., at which temperatures the enzyme shows its highest activity. When the enzymatic oxidation is carried out at the same time as the enzymatic hydrolysis using amyloglucosidase, it may be preferred to work at around 50° to 60° C., at which temperatures amyloglucosidase is most active, although they are borderline as regards the rapid denaturation of glucose oxidase and the dissolved oxygen content of the solutions undergoing hydrolysis.

a useful piece of equipment which enables this oxidation to be carried out consists of an aerobic fermenter, although it is in no way necessary for this step to take place under sterile conditions or even under rigorously aseptic conditions. The amount of enzymes used is such that the oxidation takes place in 0.5 to 24 hours.

As regards the second step of the process more generally claimed for purification of the soluble glucose polymer, a strong anionic resin is preferably used as anion exchanger, which makes it possible efficiently to bind weak acids, namely gluconic acid or other acidic glucose oxidation products which may have appeared, especially during the high-temperature heating of the latter. These strong anionic resins also make it possible very efficiently to retain the weak carboxylic acids which may have been used as catalysts for the polymerization of glucose, for example citric acid in the case of polydextrose.

The preferred resins are those which bear functional groups of quaternary amine type and even more preferably quaternary trimethylamine groups, such as the AMBERLITE IRA 900 resin marketed by Rohm and Haas.

These resins are used in their strong base or hydroxyl OH$^-$ form.

In order to increase the regeneration yield thereof with alkalis, it may be preferred to couple them with a weak anionic resin essentially bearing tertiary amino groups, such as AMBERLITE IRA 93 from the same company.

In the preferred case in which the enzymatic oxidation step has been carried out in the presence of a buffer salt or of a progressive addition of base by regulation of the pH, it will be preferred firstly to remove the cations by precipitation or ion exchange as has already been stated. In the latter case, a strong cationic resin containing sulphonated groups such as AMBERLITE IR 200C will be used, in its acidic H$^+$ form, and this step of cation exchange will thus come between the step of enzymatic oxidation and the step of deacidification.

Obviously, in all cases, the organoleptic properties and the residual colour of the products obtained may also be enhanced by complementary treatments using animal or vegetable charcoal.

Having outlined the major themes of the invention in order to reveal the scope thereof, the examples which follow, and which are featured merely for the aim of illustrating and enabling a better understanding thereof, should not be interpreted in a manner which would reduce this invention solely to these examples detailed.

EXAMPLE 1 (Preparation of the Glucose Polymer)

500 kg of anhydrous dextrose and 25 litres of water were introduced into a vitrified steel reactor fitted with a stirrer and a thermostattable jacket.

The jacket was heated until the dextrose completely dissolved, followed by addition of 10 grams of concentrated sulphuric acid diluted in a small amount of water. The reactor was then closed and subsequently depressurized in order to bring its contents progressively to a temperature of 155° C. The operation required about 8 hours for a Dextrose Equivalent equal to 11.9 to be obtained.

The paste thus obtained, which was very brown and had a strong caramel odour, was taken up in hot water in order to form a solution thereof containing about 40% solids content.

The optical density of a 40% polymer solution., measured at 420 nm in a 1 cm cell, had a value of: 0.405. This same solution had a very pronounced burnt taste and was very acrid.

EXAMPLE 2 (Comparative)

The 40% glucose polymer solution obtained in Example 1 was demineralized and decolorized at room temperature on an array of ion exchange resins comprising in series a strong cationic resin IR 200 C and then a strong anionic resin IRA 900. It will be noted here that the strong cationic resin is of no interest as regards the demineralization aspect of the polymers, the latter containing no cation at this stage. It was, however, used so that the examples are rigorously comparable with each other, because these cationic resins exert a slight decolorizing action. This demineralization-decolorization was ended when the resistivity of the solutions fell to a value below 10,000 ohms.cm.

The polymer solution thus obtained was concentrated and then atomized in order to form a yellow powder of bitter taste having an optical density of 0,160, measured under identical conditions to those of Example 1.

It gave the following physicochemical analysis:

| Dextrose Equivalent | 11.9 |
|---|---|
| Free glucose | 5.2% |
| Mw | 1620 |
| Mn | 730 |

EXAMPLE 3 (Product According to the Invention)

The 40% glucose polymer solution obtained in Example I was subjected to the action of glucose oxidase at an amount of 6250 GOX units of glucose oxidase SP 358 per kilogram of dry substrate. This reaction took place in a tank aerated with 1.5 volumes of air per volume of solution and per minute, at a pH adjusted to 5.0 by progressive addition of sodium hydroxide.

It took place at 35° C. for 16 hours, after which time the free glucose content was less than 0.2%. At this stage, the polymer solution showed an optical density of 0.52 for a 40% solids content solution. This optical density was thus higher than that of the solution obtained in Example 1. It was, however, already possible to observe that its bitterness and its burnt taste had greatly decreased.

This solution was treated with the same array of ion exchangers as that described in Example 2, until the same resistivity value was obtained. It was subsequently concentrated and then atomized in order to form a yellowish powder which was only very slightly bitter and for which the optical density of a 40% solids content solution had a value of only 0,131.

The physicochemical analysis of the powder obtained was as follows:

| Dextrose Equivalent | 7.55 |
|---|---|
| Free glucose | 0.2% |
| Mw | 1660 |
| Mn | 835 |

EXAMPLE 4 (Product According to the Invention with Enzymatic Hydrolysis Treayment)

The 40% glucose polymer solution obtained in Example. was subjected to the simultaneous action of amyloglucosidase and of glucose oxidase at amounts of 25,000 international units of amyloglucosidase (brand name AMIGAS® TS) marketed by GIST and 6250 GOX units of glucose oxidase SP 358.

This double enzymatic action was carried out in a tank aerated with 1.5 volumes of air per volume of solution per minute, at a pH adjusted to 5.0 by progressive addition of sodium hydroxide solution. The reaction was allowed to continue for 60 hours, but it is almost certain that this reaction was completed well within this time.

This solution was treated as in the case of the above examples, on an array of ion exchangers. At this stage, the optical density of a 40% solids content solution was 0.135. This demineralized solution was concentrated and atomized in order to give a yellowish powder which was only very slightly bitter.

The physicochemical analysis of the powder obtained was as follows:

| Dextrose Equivalent | 6.9 |
|---|---|
| Free glucose | trace |
| Mw | 1780 |
| Mn | 1000 |

EXAMPLE 5 (Product According to the Invention with Catalytic Hydrogenation)

The purified polymer solution obtained in Example 4 was catalytically hydrogenated using Raney nickel, at a hydrogen pressure of 50 bar, at a pH of 7.0 and at a concentration of about.40%. After filtration of the catalyst and removal of the salts on strong anionic and cationic resins, a virtually colourless syrup was obtained, of optical density equal to 0.003 under the conditions which have already been specified above. After concentration and atomization, a white powder was obtained, which was odourless and tasteless, not even sweet, giving the following analysis:

| Reducing sugars | 0.10% |
|---|---|
| Sorbitol | trace |

| | |
|---|---|
| Mw | 1750 |
| Mn | 980 |

EXAMPLE 6

Polydextrose g from Pfizer (non-demineralized), the chemical analysis of which is as follows (as a percentage of solids content):

| | |
|---|---|
| Dextrose Equivalent | 8.7 |
| Free glucose | 3.5% |
| Total glucose | 85.8% |
| Free sorbitol | 1.7% |
| Total sorbitol | 9.3% |
| Free citric acid | 0.6% |
| Total citric acid | 1.1% |
| Mw | 1740 |
| Mn | 775 | is dissolved in water to a solids content of 30%. The solution obtained is yellow and has a bitter and acidic taste.

Fifteen litres of the solution obtained are introduced into a 20-litre aerated and thermostatted reactor. The pH of this solution is adjusted to 5.6 with sodium hydroxide and the temperature is set at 35° C. The reactor is stirred at a speed of 1000 revolutions/minute and the aeration is set at 1.5 volumes of air per volume of solution and per minute, then 40 ml of enzymatic solution of glucose oxidase SP 358 from NOVO are added.

After reacting for about 90 minutes at a controlled pH of 5.6, the reactor is heated to 80° C. in order to destroy the enzyme. The solution obtained at this stage is very coloured, but its bitter taste has become less perceptible. Its acidic taste is replaced by a salty taste.

This solution was demineralized on an array of ion exchange resins identical to that used in the above examples and under the same conditions. A largely colourless solution having only a hint of bitterness was obtained. The treatment was completed using vapour-activated granulated charcoal CPG 40 from CHEMVIRON, in order to obtain an absolutely colourless solution of optical density equal to 0.002. After concentration and then atomization of this solution, a completely white powder was obtained, having no bitterness and a barely perceptible sweet taste.

This powder gave the following physicochemical analysis:

| | |
|---|---|
| D.E. | 5.2 |
| Free glucose | 0.1% |
| Total glucose | 89% |
| Free sorbitol | 1.8% |
| Total sorbitol | 9.9% |
| Free citric acid | 0% |
| Bound citric acid | 0% |
| Mw | 1850 |
| Mn | 850 |

EXAMPLE 7

Comparison of the physicochemical properties of the products according to the invention and of the products of the prior art.

a) Viscosity in Aqueous Solution:

The viscosity of the aqueous solutions of the products obtained in Examples 1 to 6 and that of polydextrose A were measureed. This measurement was carried out using a BROOKFIELD viscometer at a temperature of 20° C. on aqueous solutions at 55% solids content.

The following results were measured:

| | |
|---|---|
| Example 1 | 94 cps |
| Example 2 | 94 cps |
| Example 3 | 98 cps |
| Example 4 | 105 cps |
| Example 5 | 105 cps |
| Example 6 | 92 cps |
| Polydextrose A | 86 cps | b) Relative humidity at equilibrium

Candies sweets were made using 50% of high-purity crystallized maltitol of brand name MALTISORB® marketed by the Applicant and 50% of the products according to the invention, obtained in Examples 4 and 5. Control candies were made using 50% of maltitol and 50% of the product obtained in Example 2 and LITESSE® II polydextrose. The candies were cooked at a temperature of 160° C.

The hygroscopicity of the candies obtained was evaluated by measuring their water uptake in an atmosphere of 66% relative humidity at 20° C. after 1 and 7 days.

The following results were obtained, indicating the per cent increase in the weight of the candies:

| Comparative examples: | |
|---|---|
| Example 2, after 1 day | +1.7% |
| Example 2, after 7 days | +5.5% |
| Polydextrose LITESSE ® II, after 1 day | +1.65% |
| Polydextrose LITESSE ® II, after 7 days | +5.02% |
| Examples according to the invention: | |
| Example 4, after 1 day | +1.05% |
| Example 4, after 7 days | +3.15% |
| Example 5, after 1 day | +1.06% |
| Example 5, after 7 days | +3.20% |

It is observed that the confections, such as candies manufactured with the products according to the invention are much less hygroscopic than those manufactured with the products of the prior art, and that their relative humidity at equilibrium is higher, which makes these sweets confections, such as candies to store. It is also noted that, on account of the higher viscosity of the products according to the invention, the confections, such as candies which contain them are much less prone to cold deformation than the control confections, such as candies. They colour less on cooking and have no taste foreign to the sweet taste of the maltitol.

I claim:

1. A method for treating a soluble glucose polymer containing free glucose in order to obtain an improved glucose polymer which is substantially colorless, which has reduced bitterness, and which has a lower caloric content by reducing the original content of free glucose, said method comprising:

subjecting the polymer containing free glucose to the action of an effective amount of a glucose oxidase under conditions resulting in the oxidation of glucose to gluconic acid;

treating the polymer so obtained with an anion exchanger in hydroxyl anion form so as to bind said gluconic acid; and recovering an improved glucose polymer which is substantially colorless, which has reduced bitterness, and which has a lower caloric content than said glucose polymer containing free glucose.

2. The method according to claim 1 comprising subjecting the soluble glucose polymer containing free glucose to the action of effective amounts of starch hydrolyzing enzymes for hydroysis of said soluble glucose polymer prior to the treatment with glucose oxidase.

3. The method according to claim 1 wherein the soluble glucose polymer containing free glucose is subjected to the action of effective amounts of starch hydrolyzing enzymes for hydrolysis of said soluble glucose polymer during the treatment with glucose oxidase.

4. The method according to claim 1 comprising subjecting the improved glucose polymer to a catalytic hydrogenation in order to obtain a percentage of residual reducing sugars of less than 0.5%.

5. The method according to claim 1 comprising subjecting the soluble glucose polymer containing free glucose to the action of effective amounts of starch hydrolyzing enzymes for hydrolysis of said soluble glucose polymer prior to the treatment with glucose oxidase, and subjecting the polymer so obtained to a catalytic hydrogenation in order to obtain a percentage of residual reducing sugars of less than 0.5%.

6. Method according to claim 1 wherein the soluble glucose polymer containing free glucose is a polyglucose.

7. Method according to claim 1 wherein the soluble glucose polymsr containing free glucose is polydextrose.

8. Method according to claim 1 wherein the soluble glucose polymsr containing free glucose is a pyrodextrin.

9. Candies comprising a sugar substitute comprising the improved glucose polymer according to claim 1.

10. Food products comprising a fat substitute comprising the improved glucose polymer according to claim 1.

* * * * *